United States Patent [19]
Horan

[11] Patent Number: 5,604,955
[45] Date of Patent: Feb. 25, 1997

[54] SURGICAL LIGHTING FIXTURE COVER

[75] Inventor: Robert T. Horan, Northridge, Calif.

[73] Assignee: Graphic Controls Corporation, Chatsworth, Calif.

[21] Appl. No.: 523,259

[22] Filed: Sep. 5, 1995

Related U.S. Application Data

[63] Continuation-in-part of Ser. No. 258,498, Jun. 10, 1994, abandoned.

[51] Int. Cl.⁶ .............................. B25G 1/02; F21L 15/12
[52] U.S. Cl. ................. 16/114 R; 16/111 R; 206/438; 362/399; 362/804
[58] Field of Search ........................... 16/111 R, 114 R; 150/155; 206/223, 438; 362/399, 804

[56] References Cited

U.S. PATENT DOCUMENTS

| | | |
|---|---|---|
| D. 289,206 | 4/1987 | Scoville, Jr. et al. . |
| 4,316,237 | 2/1982 | Yamada et al. . |
| 4,559,671 | 12/1985 | Andrews et al. . |
| 4,605,124 | 8/1986 | Sandel et al. . |
| 4,739,883 | 4/1988 | Mohs et al. . |
| 4,844,252 | 7/1989 | Barron et al. . |
| 4,974,288 | 12/1990 | Reasner .................. 16/111 R |
| 5,065,296 | 11/1991 | Cude .................... 16/114 R |
| 5,156,267 | 10/1992 | Yates, Jr. et al. . |
| 5,156,456 | 10/1992 | Hoftman et al. ............ 206/438 |
| 5,273,157 | 12/1993 | Spina . |
| 5,469,600 | 11/1995 | Sandel ................... 16/111 R |
| 5,493,757 | 2/1996 | Horan et al. ............. 16/111 R |
| B1 4,844,252 | 3/1993 | Barron et al. . |

*Primary Examiner*—Jimmy G. Foster
*Attorney, Agent, or Firm*—Lyon & Lyon

[57] ABSTRACT

A disposable cover for an operating room lighting fixture handle comprises a sheath attached to a generally flat flange. At least one tab is integrally formed projecting from the flange, to provide a snap fit between the flange and a recessed area on the light fixture handle. Two covers may be conveniently packaged within a compact envelope by engaging the locking tabs of each cover with those of the other.

7 Claims, 2 Drawing Sheets

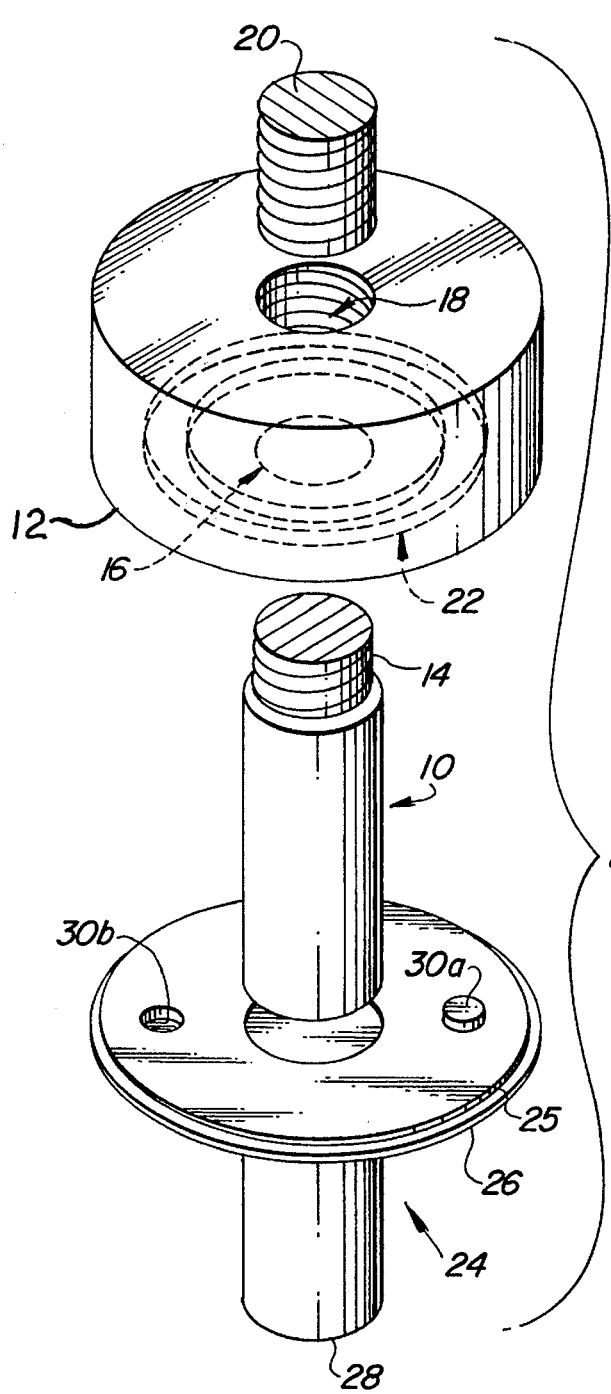
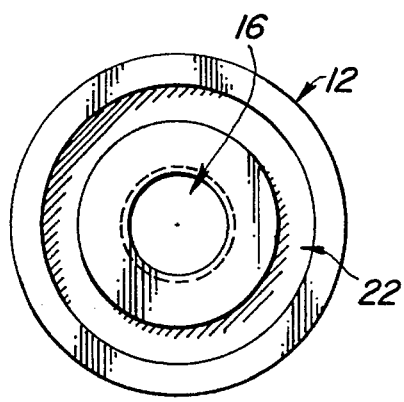
Fig. 2
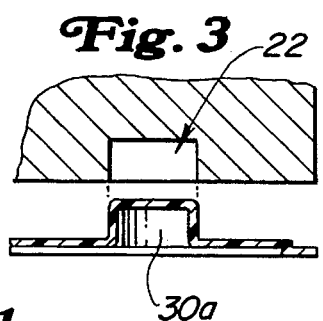
Fig. 3
Fig. 1
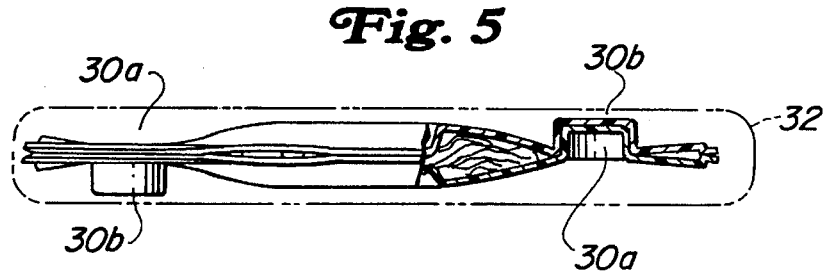
Fig. 5

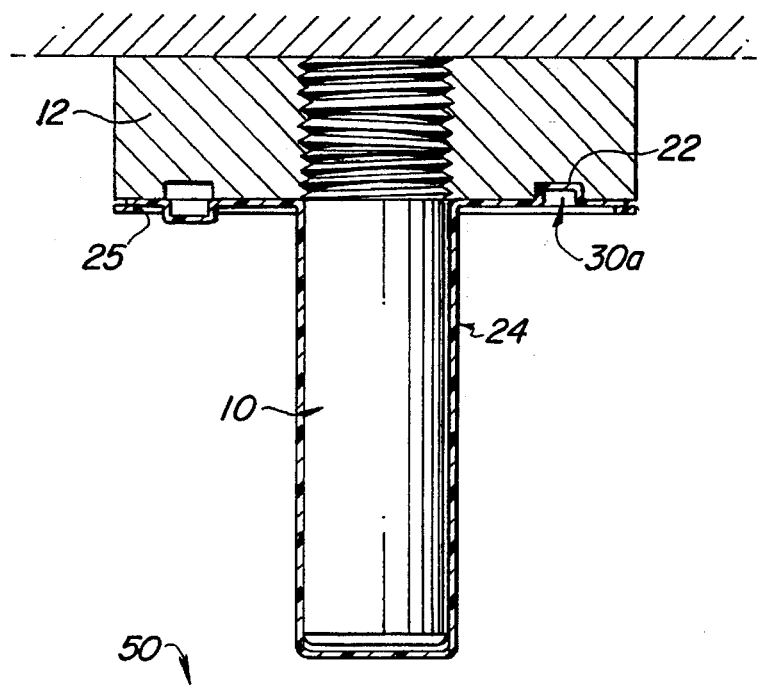
Fig. 4
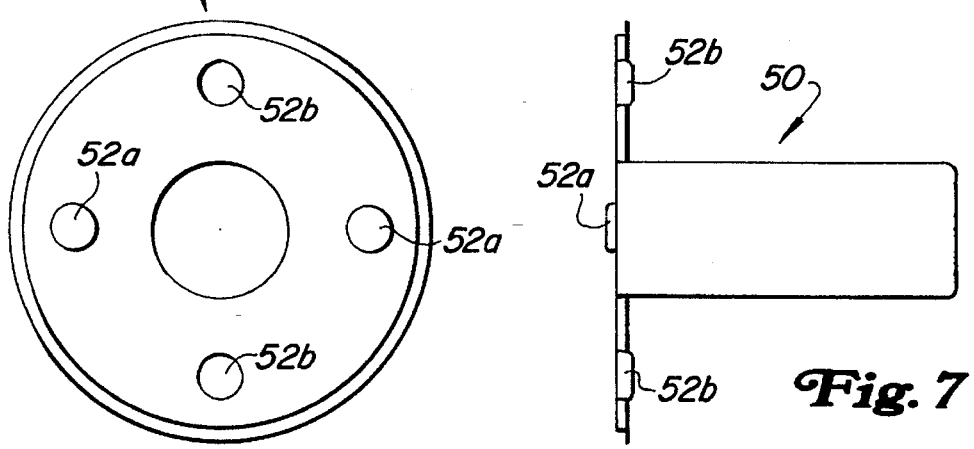
Fig. 6
Fig. 7
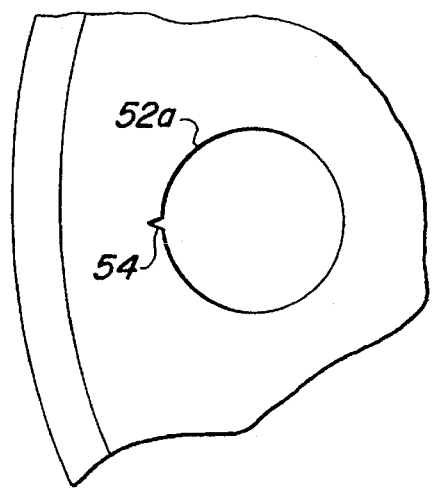
Fig. 8

SURGICAL LIGHTING FIXTURE COVER

BACKGROUND OF THE INVENTION

This application is a continuation-in-part of Ser. No. 08/258,498, filed Jun. 10, 1994 and now abandoned.

The present invention relates to a disposable sterile cover for use on a surgical lighting fixture handle.

In a typical hospital operating room, a light fixture is suspended above the operating table to provide illumination during surgical procedures. The light fixture is mounted on a movable swivel arm so that it may be adjusted by the surgical staff as needed, and includes a projecting handle by which medical personnel may grasp and move the light fixture. Typically, this projecting handle is in the middle of the lighting fixture housing and projects downwardly from the housing.

The handle must be kept sterile, so that the gloved hands of surgeons and nurses do not become contaminated when grasping the handle. One proposed method of maintaining this sterility has been the use of projecting handles that are removably attached to the light housing by screw-threaded fittings. After each surgical procedure, the projecting handle is unscrewed from the light housing and disposed of, and a new handle portion is attached prior to the next surgical procedure. However, this solution has proved to be costly. A need therefore exists for a low-cost and simple yet efficient method of maintaining the sterility of surgical lighting fixture handles.

SUMMARY OF THE INVENTION

To these ends, a disposable cover for use with a surgical lighting fixture handle includes a sheath connected to a flange, and preferably a plurality of locking tabs on the flange which interlock with tabs on a second or third cover, or with a recess in the handle.

BRIEF DESCRIPTION OF THE DRAWING FIGURES

FIG. 1 is an exploded view of a handle and cover according to the present invention;

FIG. 2 is a bottom view of the handle of FIG. 1;

FIG. 3 is an enlarged cross-section view of a portion of the disc and flange of the light handle cover of FIG. 1;

FIG. 4 is a cross-section showing a cover in place on a lighting fixture handle;

FIG. 5 is a side elevation view in part section of two covers engaged to each other, for packaging and shipping;

FIG. 6 is a plan view of a second cover embodiment;

FIG. 7 is a side elevation view thereof; and

FIG. 8 is an enlarged detail view of a locking tab of FIG. 6.

DETAILED DESCRIPTION OF THE PREFERRED EMBODIMENT

The present lighting fixture handle cover may be used on various lighting fixture handles.

As shown in FIG. 1, a lighting fixture handle comprises a grip 10 and a disc 12. The grip 10 may be attached to the disc 12 by screw threads 14 on one end of the grip 10 which may be inserted and screwed into a screw-threaded aperture 16 on the bottom of the disc 12. The grip 10 and disc 12 together form the handle of a surgical lighting fixture.

The handle may be removably attached to a lighting fixture housing via a second screw-threaded aperture 18 located on the top of the disc 12, which receives a screw-threaded projection 20 mounted on the housing. Where the handle is to be attached to a housing containing a screw-threaded aperture instead of a threaded projection, an appropriate screw-threaded adapter or bushing may be utilized, as is generally known in the art. Additionally, the disc 12 may be constructed so that the threaded apertures 16 and 18 form a single continuous threaded passageway running through the disc, as is shown in FIG. 4.

The bottom of the disc 12 includes a recessed area 22, which is shown in FIG. 1 and FIG. 2 as generally circular.

Referring to FIG. 1, a cover 24 comprises a flange 26 and a tubular sheath 28. The sheath is preferably formed of a material thinner than the flange, so that the sheath is more flexible than the flange and can be folded substantially flat against the flange. A lip or step 25 at the perimeter of the flange 26 stiffens the flange to reduce flexing. Holding tabs are provided on the flange 26. The first tab 30a projects upwardly from the upper face of the flange 26, while the second tab 30b projects downwardly from the bottom face of the flange 26. The holding tabs 30a and 30b are preferably integrally molded into the flange 26 of the cover, so that each tab forms a raised portion on one face of the flange and a recessed portion on the opposite face of the flange. The tabs are disposed on the flange 26 at locations corresponding to the location of the recess 22 on the disc 12 of the handle.

The cover 24 provides a barrier surface which a surgeon or nurse may grasp to manipulate the lighting fixture without directly contacting the surface of the handle. Accordingly, the dimensions of the cover 24, and particularly the sheath 28, are selected to allow the cover to be slid onto the handle. The diameter of the flange 26 is preferably approximately the same as the diameter of the disc 12 of the handle. When the cover 28 is in place on the handle, medical personnel grasping the handle through the sheath 28 of the cover 24 cannot accidentally contact the bottom surface of the disc 12.

The tab 30a is positioned so that it may be inserted into the recess 22 on the bottom surface of the disc 12, as shown in FIG. 4. The diameter of the tab 30a is preferably slightly larger than the diameter of the recess 22, so that the tab 30a forms a snap-fit with the recess 22. The engagement of the tab 30a with the recess 22 secures the cover 24 to the light handle, and is intended to prevent the cover 24 from accidentally separating from the handle when the lighting fixture is being manipulated. To remove the cover, the flange may be pulled away from the disc 12, causing the tab 30a to pull out the recess 22. However, the tab engages the recess 22 with sufficient strength to help hold the cover onto the handle when the handle is grabbed to move the lighting fixture. As shown in FIGS. 3 and 4, the tab 30a snaps into and is frictionally engaged in recessed portion 22 of the disc 12.

By placing the cover 24 onto the handle of the lighting fixture, a surgeon or a nurse may grip the handle through the cover 24 without coming into direct contact with the handle itself. In this way, a sterile surface is provided for grasping the lighting fixture, without the need to sterilize any part of the lighting fixture itself. The cover 24 is held in place on the handle both by friction forces created between the interior surface of the sheath 28 with the grip portion 10, as well as by the engagement of the tab 30a with the recess 22.

The number and arrangement of the holding tabs is not critical, and handle covers according to the present invention may be produced with any number of such tabs of varying shape and size located in any number of positions on the flange 26. Concomitantly, the location and shape of the recess 22 of the disc 12 and the tabs need not be precisely as illustrated herein, and may for example be formed of separate apertures on the disc 22 rather than a single continuous ring.

The cover is preferably plastic, although other materials may also be used. Preferably, the cover is formed so that the flange 26 is thicker (e.g., about 0.025 inch thick) and somewhat less flexible than the sheath 28 (which may be e.g., 0.002–0.004 inches thick).

FIG. 5 illustrates another advantageous feature of the light handle cover 24. Preferably, the sheath 28 may be folded down against the flange 26 for packaging and shipping. With the sheath 28 folded down, the entire cover 24 is substantially flat, thereby occupying very little storage space when not in use. Moreover, the tabs 30a and 30b advantageously permit two covers to be fastened together by engaging opposing locking tabs. The dimensions of the tabs holding 30a and 30b are advantageously the same. The tabs 30a and 30b are symmetrically positioned on opposite sides of the flange. As illustrated in FIG. 5, two covers may be aligned with the sheath portions contacting each other. When properly aligned, the two covers may be pressed together so that the projecting side of each tab 30a on one cover may be engaged into the recessed side of each tab 30b on the other cover, and vice-versa, to frictionally attach the two covers to each other. This arrangement advantageously permits two covers to be placed into very little space, for example, into a single container or package of small size. Consequently, the package or envelope 32 for the covers may be quite compact. This small size makes sterilization (e.g., by radiation) of the packaged covers, and storage of the package, easier. As many operating rooms have two light fixtures, the paired package of covers also provides the two covers needed, in a single sterile package. Further, the additional handling required during packaging of prior light cover handles (e.g., applying tape or a band to hold a pair of covers together) is unnecessary with the present covers.

FIGS. 6–8 show an alternative embodiment 50 having two holding tabs 52a and two holding tabs 52b, similar to tabs 30a and 30b in FIGS. 1, 3 and 4, but including vent notches 54 on the tabs 52a. The vent notches 54 allow air to vent as a tab 52b on one cover 50 is pushed into a tab 52a on a second cover. Due to the close friction fit between the tabs 52a and 52b, during packaging, air can become trapped between them, preventing their engagement. The vent notches 54 allow air to escape so the tabs 52a and 52b can be engaged together. The cover 50 having four tabs, instead of two, also allows pairs of covers to be snapped together faster as the covers require less manipulation and movement before any opposing set of tabs is aligned. Although four tabs are provided, only a two sets of tabs, preferably on opposing sides need to be used to hold a pair of covers together for packaging.

Although the particular invention has been shown in detail with reference to the preferred embodiment, various modifications may be made to it by one skilled in the art which will fall within the scope and spirit of the present invention. The invention, accordingly, should not be limited, except as set forth in the claims.

I claim:

1. A cover for a surgical lighting fixture handle, comprising:
   a generally flat disc having an outer perimeter, a top surface, and a bottom surface, and a central opening;
   a tubular and collapsible sheath having a closed bottom end and an open top end, with the open top end attached substantially perpendicularly to the bottom surface of the disc, around the central opening;
   a first holding tab on and projecting outwardly from the top surface of the disc; and
   a second holding tab on and projecting outwardly from the bottom surface of the disc.

2. The cover of claim 1, wherein the first and second holding tabs are cylindrical.

3. The cover of claim 1, wherein the first and second holding tabs are substantially identical.

4. The cover of claim 1, wherein the first and second holding tabs are equally spaced apart from the central opening.

5. The cover of claim 1, wherein the first and second holding tabs are substantially aligned on opposite sides of the central opening.

6. The cover of claim 1 further comprising a step around the outer perimeter of the disc.

7. The cover of claim 1 further comprising a vent notch on the first holding tab.

* * * * *